(12) United States Patent
Guy et al.

(10) Patent No.: US 10,202,287 B2
(45) Date of Patent: Feb. 12, 2019

(54) AMMONIA SEQUESTERING SYSTEM

(71) Applicant: The United States of America as Represented by The Secretary of The Army, Washington, DC (US)

(72) Inventors: Kathryn A. Guy, Champaign, IL (US); Martin Page, Urbana, IL (US)

(73) Assignee: THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 143 days.

(21) Appl. No.: 15/081,321

(22) Filed: Mar. 25, 2016

(65) Prior Publication Data

US 2017/0275186 A1 Sep. 28, 2017

(51) Int. Cl.
*B01J 41/02* (2006.01)
*C01B 21/02* (2006.01)
(Continued)

(52) U.S. Cl.
CPC .............. *C02F 1/281* (2013.01); *B01J 41/02* (2013.01); *C01B 21/02* (2013.01); *C02F 1/008* (2013.01);
(Continued)

(58) Field of Classification Search
CPC ...... C02F 1/281; C02F 1/46104; C02F 1/008; C02F 1/42; C02F 2201/46115; C02F 2101/16; C02F 2001/422; C02F 2303/16; C02F 2209/40; C02F 2209/14; C02F 1/28; C02F 1/46; C02F 1/461; C02F 1/586; C02F 2201/461; C02F 2201/46105; C02F 2201/4611; C02F 2201/4612; B01J 41/02; B01J 20/22; B01J 20/223; B01J 20/226; B01J 20/34; B01J 20/3433; B01J 49/00; B01J 49/30; B01J 49/50; B01J 49/80; B01J 49/85; C01B 21/02; C01B 21/04; C01B 21/0405; C01B 21/045; C01B 21/0455; C01B 21/0461; C01B 21/0466; C01B 21/0472; C01B 21/0494; G01N 21/251; G01N 33/18; G01N 33/182; G01N 33/188; C25B 1/02; C25B 1/04; C25B 1/10
(Continued)

(56) References Cited

U.S. PATENT DOCUMENTS 2,776,258 A * 1/1957 Gilliland .................. B01J 49/09
                                                        210/190
3,929,600 A * 12/1975 Hiasa ...................... C02F 1/586
                                                        205/755
(Continued)

*Primary Examiner* — Joseph W Drodge
(74) *Attorney, Agent, or Firm* — Brian C. Jones

(57) ABSTRACT

The present invention is an ammonia sequestering system including a system controller connected to a plurality of flow control valves, a feed stream extending through a system inlet, and a system outlet. The feed stream is a liquid contaminated with ammonia. At least one exchange column is located between the system inlet and the system outlet. The ion column includes an ion exchange material, a column inlet connected to one of the flow control valves, and a column outlet connected to another of the flow control valves. The system also includes a regenerant stream of an aqueous solution of sodium cations, as well as an ammonia brine stream made up of the regenerant stream and ammonia.

15 Claims, 2 Drawing Sheets

Figure 1A:
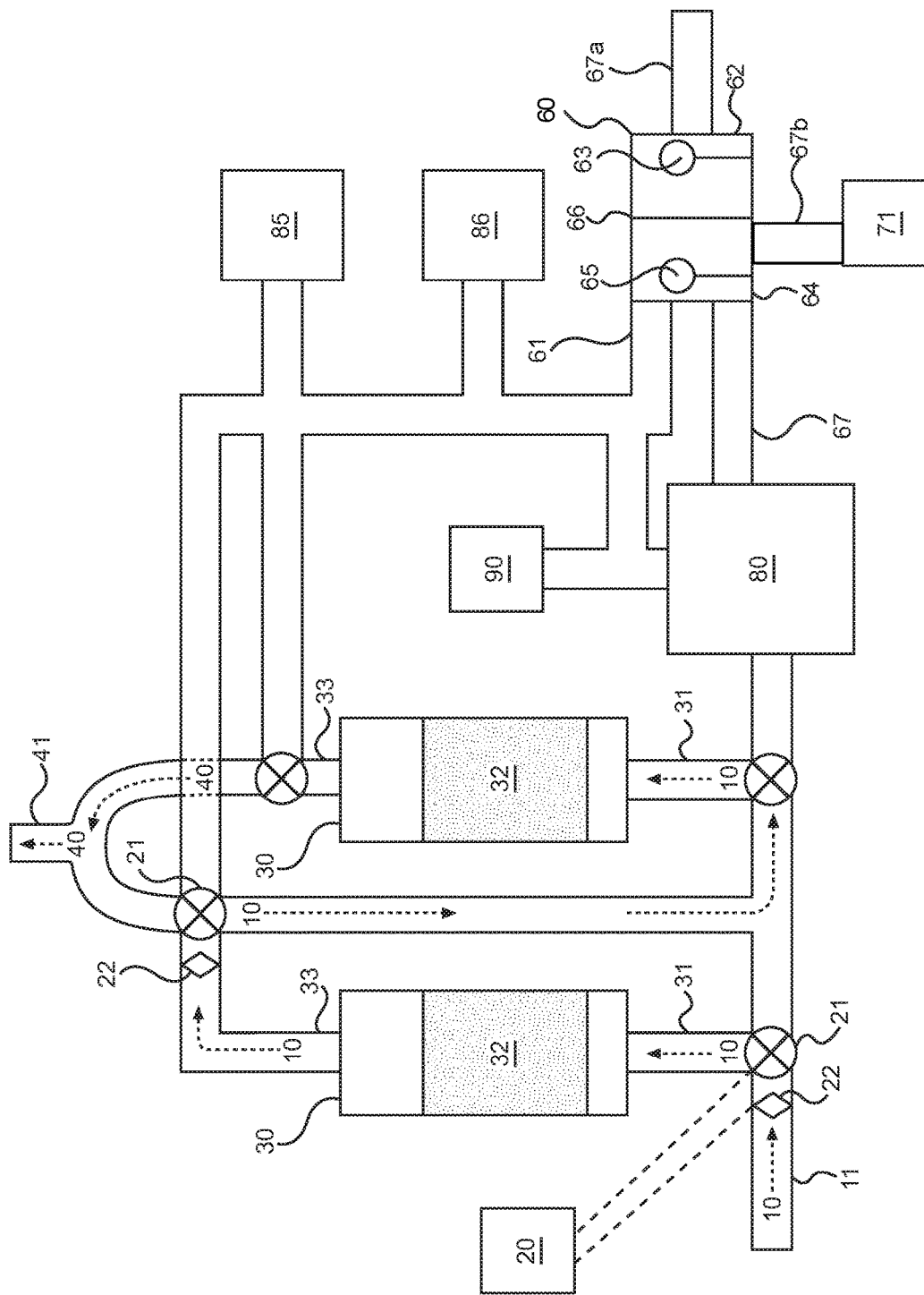

(51) Int. Cl.
*C02F 1/42* (2006.01)
*C02F 1/28* (2006.01)
*C25B 1/02* (2006.01)
*G01N 21/25* (2006.01)
*C02F 1/00* (2006.01)
*C02F 1/461* (2006.01)
*G01N 33/18* (2006.01)
*C02F 101/16* (2006.01)

(52) U.S. Cl.
CPC ............ *C02F 1/42* (2013.01); *C02F 1/46104* (2013.01); *C25B 1/02* (2013.01); *G01N 21/251* (2013.01); *C02F 2001/422* (2013.01); *C02F 2101/16* (2013.01); *C02F 2201/46115* (2013.01); *C02F 2209/14* (2013.01); *C02F 2209/40* (2013.01); *C02F 2303/16* (2013.01); *G01N 33/18* (2013.01)

(58) Field of Classification Search
USPC .. 210/660, 662, 670, 675–678, 681, 748.01, 210/805, 806, 903, 96.1, 190, 243, 257.1, 210/259, 24, 269; 204/157.4, 157.46, 204/157.52, 554, 555, 661, 666; 423/237, 423/239.1, 239.2, 356, 644, 658.3; 436/113
See application file for complete search history.

(56) References Cited

U.S. PATENT DOCUMENTS

| | | | |
|---|---|---|---|
| 4,098,690 A * | 7/1978 | Semmens | B01J 39/02 210/631 |
| 4,969,983 A * | 11/1990 | Parsi | B01D 61/445 204/524 |
| 2004/0134796 A1* | 7/2004 | Shelp | C02F 1/20 205/755 |
| 2005/0029087 A1* | 2/2005 | Kamegai | B01J 49/30 204/156 |
| 2005/0103622 A1* | 5/2005 | Jha | C02F 1/469 204/237 |
| 2006/0254969 A1* | 11/2006 | Yamanaka | B01D 15/361 210/198.2 |
| 2012/0189923 A1* | 7/2012 | Hemmes | H01M 8/0606 429/410 |
| 2014/0205505 A1* | 7/2014 | Kirollos | G01N 31/22 422/119 |

* cited by examiner

AMMONIA SEQUESTERING SYSTEM

STATEMENT REGARDING FEDERALLY SPONSORED RESEARCH OR DEVELOPMENT

The invention described herein was made by an employee of the United States Government and may be manufactured and used by the Government of the United States of America for governmental purposes without the payment of any royalties thereon or therefore.

BACKGROUND OF THE INVENTION

1. Field of Invention

This invention relates to the field of liquid purification and separation, and more specifically to purification using a regenerating ion exchange material.

2. Description of Related Art

Ammonia is a hazardous water pollutant due to its toxicity to aquatic ecosystems and its oxygen consumption during environmental degradation. Ammonia also promotes increase of phytoplankton in a water body, resulting in even greater oxygen consumption. In ammonia-polluted ecosystems, native aquatic species may die out from lack of oxygen. Furthermore, ammonia- and phytoplankton-polluted waters may be unsafe for human and animal consumption without extensive water treatment.

Ammonia is present in human, animal and industrial wastes in municipal and other wastewater processing systems. Removal of ammonia from wastewater is an energy-intensive process that has conventionally been achieved using microorganisms to convert ammonia to nitrite and then nitrate under aerobic conditions. This requires energy-intensive aeration to feed oxygen to the microorganisms, a process that is often performed in an activated sludge system during secondary wastewater treatment. Activated sludge processes generally represent nearly 50% of the energy consumption at a typical municipal wastewater treatment plant.

There is a strong interest in using anaerobic processes for wastewater treatment since they require no oxygen input. However, anaerobic systems do not degrade ammonia; rather they generate it. Current ion exchange processes are limited due to their inability to effectively dispose of ammonia-contaminated regeneration liquids. Thus, current wastewater treatment practice is still limited by energy-intensive aeration requirements to remove ammonia from wastewater.

There is an unmet need in the art for an anaerobic process for treating ammonia in wastewater.

There is a further unmet need for an energy-efficient process for treating ammonia in wastewater.

BRIEF SUMMARY OF THE INVENTION

The present invention is an ammonia sequestering system including a system controller connected to a plurality of flow control valves, a feed stream extending through a system inlet, and a system outlet. The feed stream is a liquid contaminated with ammonia. At least one exchange column is located between the system inlet and the system outlet. The ion column includes an ion exchange material, a column inlet connected to one of the flow control valves, and a column outlet connected to another of the flow control valves. The system also includes a regenerant stream of an aqueous solution of sodium cations and an ammonia brine stream made up of the regenerant stream and ammonia.

BRIEF DESCRIPTION OF SEVERAL VIEWS OF THE DRAWING(S)

Figure 1B:
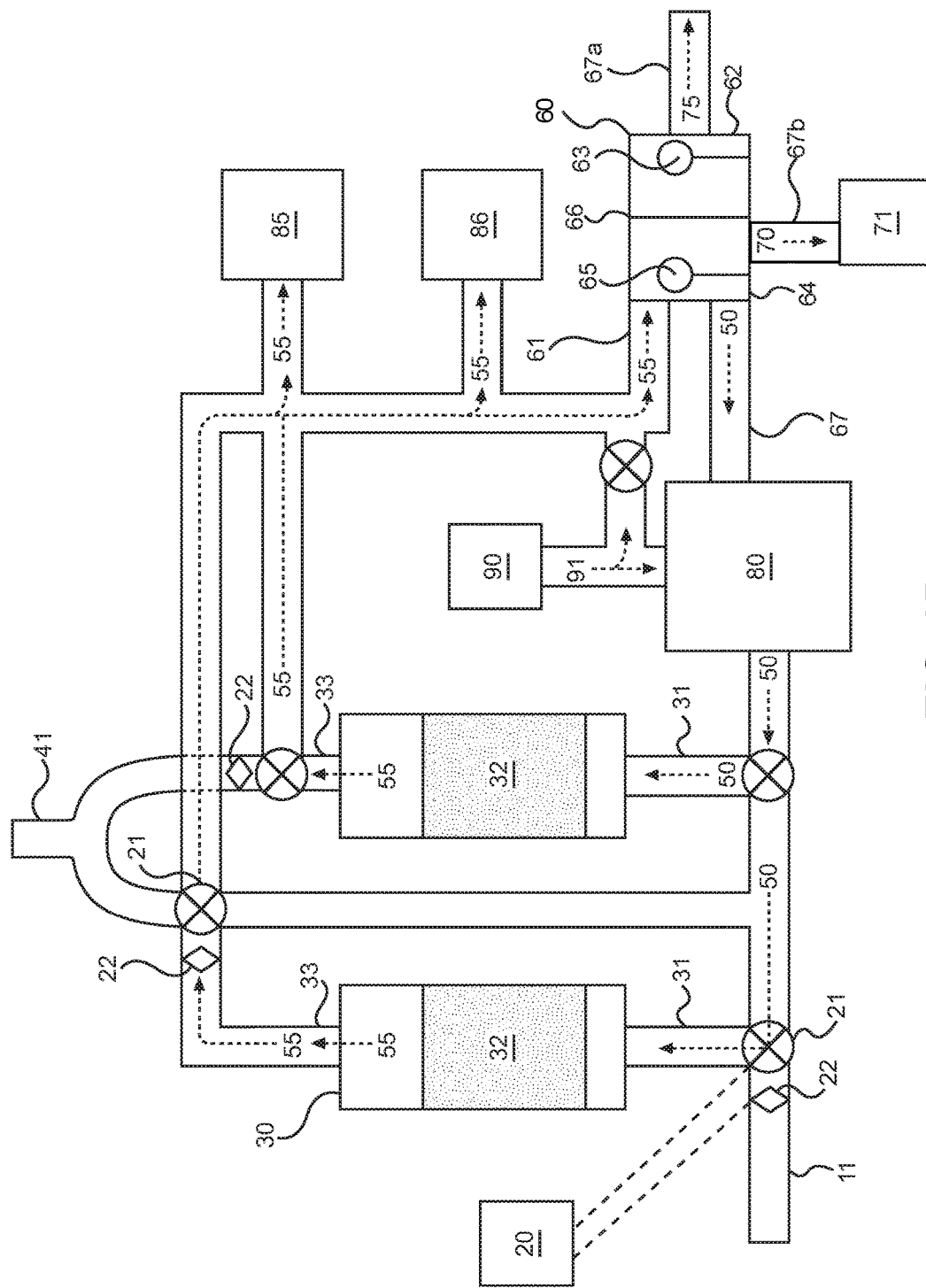

FIGS. 1a and 1b illustrate an exemplary embodiment of an ammonia sequestering system during a water treatment cycle and a regeneration cycle, respectively.

DETAILED DESCRIPTION OF THE INVENTION

FIGS. 1a and 1b illustrate an exemplary embodiment of ammonia sequestering system 100 during a water treatment cycle and a regeneration cycle, respectively.

During a water treatment cycle, ammonia sequestering system 100 receives a feed stream 10 of ammonia-contaminated water through system inlet 11. A system controller 20 directs feed stream 10 through at least one ion exchange column 30, sequestering ammonia in ion exchange column 30. A purified water stream 40 exits through system outlet 41.

During a regeneration cycle, system controller 20 directs a regenerant stream 50 through at least ion exchange column 30, removing sequestered ammonia from ion exchange column 30. A resulting ammonia brine stream 55 containing the sequestered ammonia exits ion exchange columns 30. Ammonia brine stream 55 passes directly into a processing or storage device without any intervening transfer or processing of the sequestered ammonia. In the exemplary embodiment, ammonia brine stream 55 passes into an electrolysis device 60. Electrolysis device 60 breaks down ammonia brine stream 55 into regenerant stream 50, a hydrogen gas stream 70, and a nitrogen gas stream 75. In another embodiment, ammonia brine storage chamber 85 stores ammonia brine stream 55 for later processing. In another embodiment, ammonia fuel cell 86 processes ammonia brine stream 55.

System controller 20 is an electronic processor connected to a plurality of flow control valves 21, which control flow throughout ammonia sequestering system 100. Flow control valves 21 regulate the flow or pressure of a liquid and determine whether ion exchange column 30 receives either feed stream 10 or regenerant stream 50. Flow control valves 21 also determine whether ion exchange column 30 discharges to system outlet 41, to another ion exchange column 30 or to electrolysis device 60. In certain embodiments, system controller 20 also connects to at least one ammonia sensor 22, allowing system controller 20 to process a feed stream 10 with a particularly high ammonia concentration through multiple ion exchange columns 30. In certain embodiments, ammonia sensor 22 is a colorimetric sensor.

Ammonia sequestering system 100 includes at least one ion exchange column 30. While the exemplary embodiment shows two ion exchange columns 30, more or less may be used as ammonia sequestering system 100 requires. Ion exchange material 32 is located in ion exchange column 30. Ion exchange material 32 may be, but is not limited to, natural zeolites or synthetic ion exchange materials with selective affinity for the ammonium ion. In the exemplary embodiment, ion exchange material 32 is clinoptilolite.

Each ion exchange column 30 includes a column inlet 31 selectively connected by a flow control valve 21 to either system inlet 11, a column outlet 33 of another ion exchange column 30 or a regenerant storage chamber 80. Each ion exchange column 30 also includes column outlet 33 selectively connected by another flow control valve 21 to either system outlet 41, the column inlet 31 of another ion exchange column 30 or electrolysis system 60. Depending on the cycle, column inlet 31 receives either feed stream 10 or regenerant stream 50. Depending on the cycle and the ammonia levels in feed stream 10, column outlet 33 discharges either purified water stream 40, a feed stream 10 directed to another ion exchange column 30 or ammonia brine stream 55.

Certain embodiments of ion exchange column 30 may also include ammonia sensor 22 connected to column outlet 33, allowing controller 20 to monitor levels of ammonia in any stream discharged from ion exchange column 30.

In certain embodiments with a plurality of ion exchange columns 30, both water treatment cycles and regeneration cycles occur simultaneously in different ion exchange columns 30. In other embodiments, all ion exchange columns 30 experience either a water treatment cycle or a regeneration cycle. Timing these cycles may be fixed or depend upon sensed levels of ammonia or other chemicals in ammonia sequestering system 100.

During a regeneration cycle, ammonia sequestering system 100 pumps regenerant stream 50 from regenerant storage chamber 80 into ion exchange column 30 through column inlet 31. Regenerant stream 50 stays in place for a period of time, removing absorbed ammonia from ion exchange material 32 and transforming into ammonia brine stream 55. Ammonia brine stream 55 is then displaced by another regenerant stream 50. The second regenerant stream 50 may also regenerate ion exchange material 32 or may simply drain from ion exchange column 30. Regenerant stream 50 is a concentrated aqueous solution of approximately 1 wt % to approximately 10 wt % sodium chloride. In certain embodiments, regenerant stream 50 also includes sodium hydroxide. In certain embodiments, regenerant stream 50 has a pH level of approximately 10 to approximately 14.

Electrolysis system 60 treats ammonia brine stream 55 to separate it into regenerant stream 50, hydrogen gas stream 70, and nitrogen gas stream 75. Ammonia brine stream 55 enters electrolysis system 60 through an electrolysis inlet 61. Ammonia brine stream 55 feeds into an anode chamber 62 containing an anode 63 and a cathode chamber 64 containing a cathode 65, where it undergoes catalytic conversion. A second, ammonia-free stream is not necessary for this process. An electrolysis membrane 66 separates anode chamber 62 and cathode chamber 64.

The resultant nitrogen gas stream 75 produced by anode chamber 62 discharges through a first electrolysis gas outlet 67a and vents to the atmosphere. The resultant hydrogen gas stream 70 produced by cathode chamber 64 discharges through a second electrolysis gas outlet 67b for processing in a hydrogen fuel cell 71 or storage for other energy generation systems. The resultant regenerant stream 50 discharges through electrolysis liquid outlet 68 to regenerant storage chamber 80. Because regenerant stream 50 loses sodium ions during the regeneration cycle, regenerant stream 50 may intersect and combine with an optional sodium hydroxide solution stream 91 from a hydroxide storage chamber 90 before electrolysis or during storage in regenerant storage chamber 80.

It will be understood that many additional changes in the details, materials, procedures and arrangement of parts, which have been herein described and illustrated to explain the nature of the invention, may be made by those skilled in the art within the principle and scope of the invention as expressed in the appended claims. Moreover, the term "approximately" as used herein may be applied to modify any quantitative representation that could permissibly vary without resulting in a change in the basic function to which it is related.

It should be further understood that the drawings are not necessarily to scale; instead, emphasis has been placed upon illustrating the principles of the invention.

What is claimed is:

1. An ammonia sequestering system, comprised of:
   a system controller connected to a plurality of flow control valves;
   a feed stream in communication with a system inlet, wherein said feed stream is a liquid contaminated with ammonia;
   a system outlet;
   a plurality of ion exchange columns located between said system inlet and said system outlet, wherein each of said plurality of ion exchange columns includes an ion exchange material, a column inlet connected to one of said plurality of flow control valves, and a column outlet selectively connected by one of said plurality of flow control valves to said system outlet, a column inlet of another ion exchange column, or an electrolysis system;
   a regenerant system comprising at least one regenerant storage chamber located externally to said at least one ion exchange column between said column outlet and said column inlet and a regenerant stream, wherein said regenerant stream is an aqueous solution of sodium cations;
   at least one ammonia brine storage chamber located externally to said at least one ion exchange column and connected to said column outlet, and
   the electrolysis system comprises at least one electrolysis device located externally to said at least one ion exchange column between said column outlet and said at least one regenerant storage chamber, wherein each of said at least one electrolysis devices comprise an anode chamber having an anode and a cathode chamber having a cathode, wherein an electrolysis membrane separates said anode chamber from said cathode chamber.

2. The system of claim 1, wherein said system further includes at least one ammonia sensor connected to said system controller.

3. The system of claim 2, wherein said at least one ammonia sensor is a colorimetric sensor.

4. The system of claim 2, wherein said at least one ammonia sensor comprises a sensor located between said system inlet and at least one of said plurality of flow control valves.

5. The system of claim 2, wherein said at least one ammonia sensor comprises a sensor located between said system outlet and at least one of said column outlets.

6. The system of claim 1, wherein said system further includes at least one ammonia fuel cell located externally to said plurality of ion exchange columns and connected to at least one of said column outlets.

7. The system of claim 1, wherein said at least one electrolysis devices further includes an electrolysis liquid outlet connected to said at least one regenerant storage chamber, a first electrolysis gas outlet extending from said anode chamber and a second electrolysis gas outlet extending from said cathode chamber.

8. The system of claim 1, wherein said regenerant solution has a pH of approximately 10 to approximately 14.

9. The system of claim 1, wherein said ion exchange material is selected from the group consisting of: zeolites and synthetic ion exchange material.

10. The system of claim 1, wherein said ion exchange material is clinoptilolite.

11. The system of claim 1, wherein said plurality of ion exchange columns are connected in series.

12. An ammonia sequestering method comprising the steps of:
providing a system controller connected to a plurality of flow control valves to control fluid flow in the following steps;
a treatment cycle comprising introducing a feed stream into a system inlet and further into a plurality of ion exchange columns located between said system inlet and a system outlet, wherein each of said plurality of ion exchange columns includes an ion exchange material, a column inlet connected to one of said plurality of flow control valves, and a column outlet selectively connected by one of said plurality of flow control valves to said system outlet, a column inlet of another ion exchange column, or an electrolysis system, wherein said feed stream is a liquid contaminated with ammonia, said ion exchange material sequestering said ammonia, and discharging a purified stream from a system outlet; and
a regeneration cycle comprising directing a regenerant stream comprising an aqueous solution of sodium cations from at least one regenerant storage chamber located externally to said plurality of ion exchange columns and between said column outlet and said column inlet through said plurality of ion exchange columns to remove said sequestered ammonia from said ion exchange material,
providing at least one ammonia brine storage chamber located externally to said plurality of ion exchange columns and connected to said column outlet to store an ammonia brine stream, wherein said ammonia brine stream is made up of said regenerant stream and ammonia, and
treating said ammonia brine stream to form said regenerant stream, a hydrogen gas stream and a nitrogen gas stream by passing said ammonia brine stream into said electrolysis system, said electrolysis system comprising at least one electrolysis device located externally to said plurality of ion exchange columns between said column outlet and said at least one regenerant storage chamber, wherein each of said at least one electrolysis devices comprise an anode chamber having an anode, said nitrogen gas stream produced by said anode chamber, and a cathode chamber having a cathode, said hydrogen stream being produced by said cathode chamber, wherein an electrolysis membrane separates said anode chamber from said cathode chamber.

13. The method of claim 12, wherein said regenerant solution is a solution of water and sodium chloride.

14. The method of claim 13, wherein said regenerant solution includes approximately 90 wt % to approximately 99 wt % water and approximately 1 wt % to approximately 10 wt % sodium chloride.

15. The method of claim 13, wherein said regenerant solution further comprises sodium hydroxide.

* * * * *